(12) United States Patent
Sato et al.

(10) Patent No.: US 7,135,592 B2
(45) Date of Patent: Nov. 14, 2006

(54) PROCESS FOR PRODUCING POLYFLUOROALKYL ESTER OF UNSATURATED CARBOXYLIC ACID

(75) Inventors: Katsuyuki Sato, Kitaibaraki (JP); Keisuke Kokin, Kitaibaraki (JP); Sunao Ikeda, Kitaibaraki (JP); Kimihiko Urata, Kitaibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 0 days.

(21) Appl. No.: 11/191,398

(22) Filed: Jul. 28, 2005

(65) Prior Publication Data

US 2006/0025625 A1    Feb. 2, 2006

(30) Foreign Application Priority Data

Jul. 30, 2004    (JP) ............................. 2004-223054

(51) Int. Cl.
*C07C 69/52*    (2006.01)
*C07C 67/38*    (2006.01)

(52) U.S. Cl. ...................................... 560/190; 560/223

(58) Field of Classification Search .................... None
See application file for complete search history.

(56) References Cited

FOREIGN PATENT DOCUMENTS

| | | | |
|---|---|---|---|
| GB | 1266408 | * | 3/1972 |
| JP | 59-181239 | * | 10/1984 |
| JP | 62-92914 | | 10/1986 |
| JP | 63-210115 | | 2/1987 |
| JP | 5-51417 | | 8/1991 |

OTHER PUBLICATIONS

Inhibition of Gap Junctional Intercellular Communication by Perfluorinated Fatty Acids is Dependent on the Chain Length of the Fluorinated Tail, Brad L. Upham, et al, Int. J. Cancer: 78, 491-495 (1998).

* cited by examiner

*Primary Examiner*—Paul A. Zucker
(74) *Attorney, Agent, or Firm*—Butzel Long

(57) ABSTRACT

A polyfluoroalkyl ester of unsaturated carboxylic acid is produced in high yield in a more simple reactor and with much more reduction in the waste than the conventional process based on esterification reaction by subjecting a polyfluoroalkanol represented by the following general formula:

$$Rf{-}R{-}OH$$

where Rf is a polyfluoroalkyl group having 1–6 carbon atoms and R is an alkylene group having 1–6 carbon atoms, and an unsaturated carboxylic acid to dehydration reaction in a fluorine-containing solvent in the presence of an acid catalyst and a polymerization inhibitor.

13 Claims, No Drawings

PROCESS FOR PRODUCING POLYFLUOROALKYL ESTER OF UNSATURATED CARBOXYLIC ACID

BACKGROUND OF THE INVENTION

1) Field of the Invention

The present invention relates to a process for producing a polyfluoroalkyl ester of unsaturated carboxylic acid, and more particularly to a process for producing a polyfluoroalkyl ester of unsaturated carboxylic acid useful as a starting monomer for polymers or as a starting compound for surfactants.

2) Related Art

Polyfluoroalkyl esters of unsaturated carboxylic acids, typically polyfluoroalkyl (meth)acrylate, have been hereto produced in an industrial scale as starting monomers for polymers with such characteristics as high transparency, chemical resistance, water- and oil-repellency, antifouling property, etc. due to specific nature of fluorine atoms contained in the molecules or as a starting compound for surfactants. However, due to now raised problems as to toxicity, accumulation, etc. of fluorotelomer, typically perfluorooctanoic acid (PFOA) and perfluorooctansulfonic acid (PFOS), it has been desired to substitute compounds with less toxicity and accumulation, but with equivalent characteristics.

International Journal of Cancer 78, issue 4, pages 491–495 (1998) reports that Rf groups having 2–5 or 16, 18 carbon atoms has a low inhibiting effect on intercellular information transmission performance (GJIC).

J. Fluorine Chemistry 5920 (2003), pages 1–20, discloses that Rf groups having carbon atoms around $C_3$, which must be less than $C_8$, can give a satisfactory surface activity, when formed into bifunctional compounds.

On the other hand, a process for producing carboxylic acid esters generally includes those based on dehydration condensation of carboxylic acid and alcohol in the presence of an acid catalyst or on chemical dehydration condensation in the presence of a dehydrating agent. Furthermore, a process based on dehydrohalogenation of carboxylic acid halide and alcohol is well known.

A process for producing a polyfluoroalkyl ester of unsaturated carboxylic acid includes those based on dehydration condensation of an unsaturated carboxylic acid and a polyfluoroalkanol in the presence of an acid catalyst such as p-toluenesulfonic acid, etc. with heating, using a non-polar solvent such as toluene, etc. as a water-azeotropic solvent, while distilling off the generated water, as disclosed in JP-A-63-210115 and JP-A-05-051417.

In these processes, however, polyfluoroalkanol is often inevitably removed to the outside of the reaction system due to the azeotropic boiling of polyfluoroalkanol and the dehydration solvent, and thus the expensive polyfluoroalkanol must be added in excess to the unsaturated carboxylic acid. Furthermore, the reaction must be carried out at elevated temperatures, and thus it is hard to suppress formation of polymers even in the presence of a polymerization inhibitor. Even in the industrial scale production, complicated apparatuses will be required for the removal of the generated water. Furthermore, in the recycle of used solvent for reuse, a large amount of expenditure will be required for the recycle for reuse, etc. as a problem due to the control of water content in the solvent or contamination of the solvent with impurities and by-products.

Still furthermore, in these processes, polyfluoroalkanol with a high acidity such as $RfCH_2OH$ has a very low reaction rate, resulting in occurrence of many side reactions, and thus it is very difficult to produce the desired product in high purity.

JP-A-62-92914 discloses a process based on dehydration condensation of itaconic acid and 1,1,1,3,3,3-hexafluoroisopropanol in an aprotonic polar solvent, using N,N'-dicyclohexylcarbodiimide (DCC) as a dehydrating agent, where the dehydrating agent DCC, though expensive, must be used in an equal amount to that of the alcohol, and also is impossible to recycle for the reuse, and thus generation of a large amount of wastes, etc. will inevitably occur as problems.

Other processes are also available, which are based on conversion of unsaturated carboxylic acids to carboxylic acid halides by various halogenating agents, followed by reaction with alcohols in the presence of a base, where an additional step of conversion to carboxylic acid halides as a starting material is required, that is, one more step is required in the process. Furthermore, the carboxylic acid halides are easy to hydrolize in the presence of water, resulting in strict water content control of the solvent to be used, etc. Hydrogen halides generated by the hydrolysis are highly corrosive, and thus the apparatuses must be made from expensive anti-corrosive materials, etc. Generation of a large amount of halides of the base used leads to a large amount of expenditure on the waste treatment.

SUMMARY OF THE INVENTION

An object of the present invention is to provide a process for producing a polyfluoroalkyl ester of unsaturated carboxylic acid useful as a starting monomer for polymers or as a starting compound for surfactants at a relatively low temperature in high yield with less wastes in a simple reactor.

The object of the present invention can be attained by dehydration reaction of a polyfluoroalkanol represented by the following general formula:

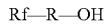

Rf—R—OH where Rf is a polyfluoroalkyl group having 1–6 carbon atoms, and R is an alkylene group having 1–6 carbon atoms, and an unsaturated carboxylic acid in a fluorine-containing solvent in the presence of an acid catalyst and a polymerization inhibitor.

The present process can produce a polyfluoroalkyl ester of unsaturated carboxylic acid in higher yield in a more simple reactor and with much more reduction in the waste than the conventional process based on esterification reaction.

DETAILED DESCRIPTION OF THE INVENTION

Polyfluoroalkanol Rf—R—OH as one component of the starting compounds has an Rf group selected from polyfluoroalkyl groups, preferably perfluoroalkyl groups, having 1–6 carbon atoms and an R group selected from alkylene groups having 1–6 carbon atoms, and from the viewpoints of easy availability, toxicity and accumulation preferably those with on Rf group having not more than 4 carbon atoms and an R group having 1 or 2 carbon atom are used. For example, 2,2,2-trifluoroethanol ($CF_3CH_2OH$), 2,2,3,3-tetrafluoropropanol ($HCF_2CF_2CH_2OH$), 2,2,3,3,3-pentafluoropropanol ($CF_3CF_2CH_2OH$), 3,3,4,4,4-pentafluorobutanol ($CF_3CF_2CH_2CH_2OH$), 2,-2,3,4,4,4-hexafluorobutanol ($CF_3CHFCF_2CH_2OH$), 2,2,3,3,4,4,5,5-nonafluoropentanol ($CF_3CF_2CF_2CF_2CH_2OH$), 2,2,3,3,4,4,5,5-octafluoropentanol (HC—F$_2$CF$_2$CF$_2$CF$_2$CH$_2$OH), 3,3,4,4,5,5,6,6,6-nonafluorohexanol (CF$_3$CF$_2$CF$_2$CF—$_2$CH$_2$CH$_2$OH), etc. are included, but polyfluoroalkylethanol (RfCH$_2$CH$_2$OH) is costwise relatively expensive and is now industrially less practical. Thus, polyfluoroalkylmethanol (RfCH$_2$OH) is preferably used.

Unsaturated carboxylic acid, which reacts with polyfluoroalkanol, includes monofunctional acrylic acid, methacrylic acid and crotonic acid, and bifunctional itaconic acid, maleic acid and fumaric acid, etc., and from the viewpoints of fluorine content and performance development bifunctional unsaturated carboxylic acids are preferably used.

Reaction of unsaturated carboxylic acid and polyfluoroalkanol can be carried out by adding 0.5–1.5 parts by mole, preferably 0.95–1.05 parts by mole, of the alkanol on the basis of one part by mole of the carboxylic acid group in the unsaturated carboxylic acid. Different from the conventional process, the present process has a distinguished characteristic in unnecessity of using expensive polyfluoroalkanol in excess.

Solvent for use in the reaction must have a solubility of water in the solvent of not more than 1%, and at least one fluorine atom in the molecule. For example, chlorofluorocarbons, perfluorocarbons, hydrochlorofluorocarbons, hydrofluorocarbons, etc. are included. From the viewpoints of post-treatment after the reaction and easy separation, R-225 (dichloropentafluoropropane) is preferably used. The solvent is used in a proportion of 1–5 parts by weight, preferably 2–3 parts by weight, on the basis of one part by weight of polyfluoroalkanol.

Acid catalyst herein used includes strong acids such as concentrated sulfuric acid, p-toluenesulfonic acid, methanesulfonic acid, etc. Preferably, concentrated sulfuric acid is used. The acid catalyst is used in a proportion of 0.5–2 parts by weight, preferably 1.2–1.3 parts by weight, on the basis of one part by weight of polyfluoroalkanol. The acid catalyst used can be recycled for reuse by removing the product, unreacted raw materials, etc. by distillation, etc.

In addition to the afore-mentioned components, a polymerization inhibitor such as hydroquinone, hydroquinone monomethyl ether, phenothiazine, etc. is added thereto to conduct reaction. The polymerization inhibitor is used in a proportion of 0.01–1 wt. %, preferably 0.1–0.3 wt. %, on the basis of unsaturated carboxylic acid.

Reaction can be carried out under any of subatmosperic pressure, atmospheric pressure, and superatmospheric pressure, and at a temperature of 20–100° C., preferably 30–50° C. During the reaction, an appara-tus for discharging condensed water to the outside of the reaction system can be also used, but usually not used to avoid eventual discharging of the raw materials to the outside of the reaction system.

After the reaction, the setting-separated, desired product phase is recovered and joined with another desired product phase recovered from the catalyst layer by distillation, followed by neutralization-washing with an aqueous alkaline solution of sodium hydrogen carbonate, sodium carbonate, etc., dehydration-drying, and distillation-purification, whereby the desired polyfluoroalkyl ester of unsaturated carboxylic acid can be obtained.

PREFERRED EMBODIMENTS OF THE INVENTION

The present invention will be described in detail below, referring to Examples.

EXAMPLE 1

Production of bis(2,2,3,3,3-pentafluoropropyl)itaconate 300 g of 2,2,3,3,3-pentafluoropropanol, 130 g of itaconic acid, 1.0 g of hydroquinone, and 470 ml of R-225 were charged into a glass reactor of 1 L capacity provided with a magnet stirrer, a thermometer, a dropping funnel, and a reflux condenser, and the reactor is cooled with water. Then, 385 g of concentrated sulfuric acid (concentration: 96%, specific gravity: 1.84) was dropwise slowly added to the reactor. After the dropwise addition, the reactor was stirred at room temperature for about one hour, and further stirred with heating at an inside temperature of 45° C. for 20 hours. The reaction mixture was cooled, and then the organic phase and the sulfuric acid phase as separated each in the discrete layers, were separated from each other, the organic phase was joined with the fraction recovered from the sulfuric acid phase by distillation, and neutralized and washed with an aqueous saturated NaHCO$_3$ solution, followed by dehydration and drying over anhydrous MgSO$_4$, whereby crude ester was obtained. By subjecting the crude ester to solvent evaporation and subatmospheric distillation, 305 g of a fraction having a boiling point of 60–62° C./1 mmHg was obtained.

It was found by H-NMR: TMS δ 6.4 (1H), 6.0 (1H), 4.7 (2H), 4.8 (2H) and 3.6 (2H), and by F-NMR: CFCl$_3$ δ −83(CF$_3$) and −122(CF$_2$) that the resulting compound was the desired bis(2,2,3,3,3,-pentafluoropropyl) itaconate. Yield of bis(2,2,3,3,3-pentafluoropropyl) itaconate was found to be 77% (on the basis of itaconic acid).

COMPARATIVE EXAMPLE

Production of bis(2,2,3,3,3-pentafluoropropyl)itaconate 300 g of 2,2,3,3,3-pentafluoropropanol, 300 ml of cyclohexane, 1.0 g of hydroquinone, and 3.0 g of p-toluenesulfonic acid•monohydrate were charged into a glass reactor of 1 L capacity provided with a magnet stirrer, a thermometer, a dropping funnel, and a Dienstark moisture quantitative determining apparatus, and the reactor was heated up to the inside temperature of 85° C. After refluxing of cyclohexane, a solution containing 130 g of itaconic acid in 50 ml of cyclohexane was charged to the reactor through the dropping funnel. After the dropwise addition, the reactor was stirred for 5 hours with heating until any condensation water no more flowed out. Cyclohexane was distilled off the reaction mixture by simple distillation, followed by subatmospheric distillation, whereby 210 g of a fraction having a boiling point of 60–62° C./1 mmHg was obtained. Yield of bis(2,2,3,3,3-pentafluoropropyl) itaconate was found to be 53% (on the basis of itaconic acid).

EXAMPLE 2

Production of 2,2,3,3,3-pentafluoropropyl acrylate 600 g of 2,2,3,3,3,-pentafluoropropanol, 288 g of acrylic acid, 0.5 g of hydroquinone, and 1,000 ml of R-225 were charged into a glass reactor of 3 L capacity, provided with a magnet stirrer, a thermometer, a dropping funnel, and a reflux condenser. The reactor was ice-cooled, and then 770 g of concentrated sulfuric acid was dropwise slowly added thereto. The reactor was stirred at room temperature for about one hour and then further stirred with heating at the inside temperature of 45° C. for 20 hours. The reaction mixture was cooled, and the organic phase and the sulfuric acid phase as separated each into the discrete layers, were separated from each other. The organic phase was joined with the fraction recovered from the sulfuric acid phase by distillation and neutralized and washed with an aqueous saturated NaHCO$_3$ solution, followed by dehydration-drying over anhydrous MgSO$_4$, whereby crude ester was obtained. By subjecting the crude ester to solvent evaporation and subatmospheric distillation, 654 g of a fraction having a boiling point of 36–37° C./100 mmHg was obtained.

It was found by H-NMR: TMS δ 6.5(1H), 6.2(1H), 6.0(1H) and 4.8(2H) and by F-NMR: CFCl$_3$ δ –83(CF$_3$) and –122(CF$_2$) that the resulting compound was the desired 2,2,3,3,3-pentafluoropropyl acrylate. Yield of 2,2,3,3,3-pentafluoropropyl acrylate was found to be 80% (on the basis of acrylic acid).

EXAMPLE 3

Production of 2,2,3,3,3-pentafluoropropyl methacrylate

In Example 2, 344 g of methacrylic acid was used in place of acrylic acid, whereby 663 g of a fraction having a boiling point of 45–46° C./45 mmHg was obtained.

It was found by H-NMR: TMS δ 6.1(1H), 5.7(1H), 4.8(2H) and 1.9(3H), and by F-NMR: CFCl$_3$ δ –83(CF$_3$) and –122 (CF$_2$) that the resulting compound was the desired 2,2,3,3,3-pentafluoropropyl methacrylate. Yield of 2,2,3,3,3-pentafluoropropyl methacrylate was found to be 76% (on the basis of methacrylic acid).

What is claimed is:

1. A process for producing a polyfluoroalkyl ester of unsaturated carboxylic acid, which comprises subjecting a polyfluoroalkanol represented by the following general formula:

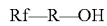

wherein Rf is a polyfluoroalkyl group having 1–6 carbon atoms, and R is an alkylene group having 1–6 carbon atoms, and an unsaturated carboxylic acid to dehydration reaction in a fluorine-containing reaction solvent in the presence of an acid catalyst and a polymerization inhibitor, said fluorine-containing reaction solvent being a solvent that has a water solubility in the solvent of not more than 1%.

2. A process according to claim 1, wherein the polyfluoroalkanol is polyfluoroalkylmethanol.

3. A process according to claim 2, wherein the polyfluoroalkylmethanol is 2,2,3,3,3-pentafluoropropanol.

4. A process according to claim 1, wherein the unsaturated carboxylic acid is monofunctional acrylic acid, methacrylic acid or crotonic acid.

5. A process according to claim 1, wherein the unsaturated carboxylic acid is bifunctional itaconic acid, maleic acid or fumaric acid.

6. A process according to claim 1, where the polyfluoroalkanol is used in a proportion of 0.5–1.5 parts by mole on the basis of one part by mole of the carboxylic acid group in the unsaturated carboxylic acid.

7. A process according to claim 1, wherein the polyfluoroalkanol is used in a proportion of 0.95–1.05 parts by mole on the basis of one part by mole of the carboxylic acid group in the unsaturated carboxylic acid.

8. A process according to claim 1, wherein during the dehydration reaction the reaction is carried out without discharging the generated condensation water to the outside of reaction system.

9. A process according to claim 1, wherein the fluorine-containing reaction solvent is chlorofluorocarbons, perfluorocarbons, hydrochlorofluorocarbons or hydrofluorocarbons.

10. A process according to claim 9, wherein the fluorine-containing reaction solvent is dichloropentafluoropropane.

11. A process according to claim 1, wherein the acid catalyst is concentrated sulfuric acid.

12. A process according to claim 1, wherein the acid catalyst is used in a proportion of 0.5–2 parts by weight on the basis of one part by weight of the polyfluoroalkanol.

13. Bis(2,2,3,3,3-pentafluoropropyl) itaconate.

* * * * *